(12) United States Patent
Hada et al.

(10) Patent No.: US 6,388,101 B1
(45) Date of Patent: May 14, 2002

(54) CHEMICAL-SENSITIZATION PHOTORESIST COMPOSITION

(75) Inventors: Hideo Hada, Hiratsuka; Kazufumi Sato, Sagamihara; Hiroshi Komano, Kanagawa-ken, all of (JP)

(73) Assignee: Tokyo Ohka Kogyo Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/562,458

(22) Filed: May 2, 2000

Related U.S. Application Data

(62) Division of application No. 09/012,827, filed on Jan. 23, 1998.

(30) Foreign Application Priority Data

Jan. 24, 1997 (JP) .............................. 9-11581

(51) Int. Cl.[7] .......................... C07D 305/12
(52) U.S. Cl. .................................... 549/318
(58) Field of Search ........................ 549/318

(56) References Cited

U.S. PATENT DOCUMENTS 4,276,218 A * 6/1981 Lantzsch .................... 549/318
4,882,434 A * 11/1989 Yoshioka .................... 549/318

FOREIGN PATENT DOCUMENTS

| JP | 57-141644 | 9/1982 |
|----|-----------|--------|
| JP | 4-39665 | 2/1992 |
| JP | 5-265212 | 10/1993 |
| JP | 5-346668 | 12/1993 |
| JP | 7-181677 | 7/1995 |
| JP | 9-90637 | 4/1997 |

OTHER PUBLICATIONS

Thomas et al, CA118:233531, 1993.*
Sato et al, CA129:267915, 1998.*
Uetani et al, CA129:154694, 1998.*
Zamzow et al, CA121:109776, 1994.*
Nozaki et al, CA130:132895, 1999.*
Sato et al, CA130:73851, 1998.*
Nozaki et al, CA127:227270, 1997.*
Zamzow et al, CA121:135071, 1994.*

* cited by examiner

*Primary Examiner*—Deborah C. Lambkin
(74) *Attorney, Agent, or Firm*—Wenderoth, Lind & Ponack, LLP

(57) ABSTRACT

Proposed is a chemical-sensitization positive-working photoresist composition for photolithographic patterning in the manufacture of semiconductor devices having high transparency even to ultraviolet light of very short wavelength such as ArF excimer laser beams of 193 nm wavelength to exhibit high photosensitivity and capable of giving a patterned resist layer with high pattern resolution. The composition comprises (A) a resinous ingredient which is subject to an increase of the solubility in an aqueous alkaline developer solution in the presence of an acid and (B) a radiation-sensitive acid-generating compound. Characteristically, the resinous ingredient as the component (A) is a (meth)acrylic copolymer of which from 20% to 80% by moles of the monomeric units are derived from a (meth) acrylic acid ester of which the ester-forming group has a specific oxygen-containing heterocyclic ring structure.

4 Claims, No Drawings

CHEMICAL-SENSITIZATION PHOTORESIST COMPOSITION

This is a divisional application of Ser. No. 09/012,827, filed Jan. 23, 1998.

BACKGROUND OF THE INVENTION

The present invention relates to a novel chemical-sensitization photoresist composition or, more particularly, to a positive-working chemical-sensitization photoresist composition used in the photolithographic patterning in the manufacture of various kinds of electronic devices.

Chemical-sensitization photoresist compositions in the prior art usually contain a resinous ingredient having high transparency to the KrF excimer laser beams of 248 nm wavelength which is mainly a polyhydroxystyrene resin, optionally, substituted for the hydroxyl groups therein by acid-dissociable solubility-reducing groups. It is a trend in recent years, however, that the KrF excimer laser beam as the exposure light is increasingly under replacement with an ArF excimer laser beam having a shorter wavelength of 193 nm in order to comply with the requirements toward finer and finer patterning in the manufacture of modern semiconductor devices.

When the photolithographic patterning process is conducted with the ArF excimer laser beams as the exposure light source, the polyhydroxystyrene-based resinous ingredient is no longer suitable as the resinous ingredient of the photoresist compositions because of the low transparency of the resin to the light of 193 nm wavelength due to the aromatic ring structure contained in the resin. In this regard, acrylic resins having no aromatic structure are highlighted as a substitute for the polyhydroxystyrene resins while acrylic resins in general have a disadvantage of low resistance against dry etching.

It is known that an acrylic resin can be imparted with increased resistance against dry etching when monomeric units derived from an alicyclic alkyl ester of acrylic acid are introduced into the molecular structure of the acrylic resin. For example, proposals have been made, in Japanese Patent Kokai 4-39665, for a polymer of an acrylic ester having a skeleton of adamantane in the ester-forming group and, in Japanese Patent Kokai 5-265212, for a copolymer of an acrylic ester having a skeleton of adamantane in the ester-forming group and tetrahydropyranyl acrylate.

Although improvements in the transparency and resistance against dry etching can be accomplished to some extent for an acrylic resin by the introduction of the monomeric units derived from an acrylic ester having a skeleton of adamantane, the improvements obtained thereby are still not quite satisfactory if not to mention the low availability and hence expensiveness of such an acrylic ester having a skeleton of adamantane along with a disadvantage of low photosensitivity of the photoresist composition formulated with such an acrylic resin not to give an excellent result of patterning.

While the photolithographic patterning process by using ArF excimer laser beams as the exposure light has an important target to form a very finely patterned resist layer with extremely fine pattern resolution of 0.2 μm or even finer, such extremely fine patterning is sometimes accompanied by a defect of pattern falling due to deficiency in the adhesion between the substrate surface and the resist layer formed thereon. As a remedy for this drawback, proposals have been made for an acrylic resin containing monomeric units derived from an acrylic ester having an oxygen-containing heterocyclic group such as 3-oxocyclohexyl acrylate (Japanese Patent Kokai 5-346668) and γ-butyrolactone (Japanese Patent Kokai 7-181677).

When such an acrylic resin, into which the monomeric units of an acrylic acid ester having an oxygen-containing heterocyclic group are introduced, is used as a resinous ingredient of a photoresist composition to be used for patterning exposure with ArF excimer laser beams, however, a patterned resist layer having high fidelity cannot be obtained in the puddle development treatment as a major current in the manufacture of semiconductor devices due to insufficient affinity of the photoresist composition with the aqueous alkaline solution as the developer solution, even though an improvement to some extent can be obtained in the adhesion of the photoresist layer to the substrate surface. Therefore, one of the important subject matters in the technological field of photoresist compositions is to develop a photoresist composition for patterning exposure to light such as the ArF excimer laser beams exhibiting excellent adhesion between the resist layer and the substrate surface and having high affinity with an aqueous alkaline developer solution suitable for a puddle development treatment.

SUMMARY OF THE INVENTION

The present invention accordingly has an object to provide, in view of the above described situations in the prior art, a chemical-sensitization photoresist composition having high transparency to the ArF excimer laser beams and suitable for a puddle development treatment with high affinity to an aqueous alkaline developer solution to give a patterned resist layer with high photosensitivity having an excellently orthogonal cross sectional profile and exhibiting excellent adhesion to the substrate surface and resistance against dry etching.

Thus, the present invention provides a chemical-sensitization positive-working photoresist composition which comprises, as a uniform solution in an organic solvent:

(A) 100 parts by weight of an acrylic resin of which the solubility in an aqueous alkaline solution is subject to an increase in the presence of an acid; and (B) from 0.5 to 30 parts by weight of a radiation-sensitive acid-generating agent capable of releasing an acid when irradiated with actinic rays, the acrylic resin as the component (A) being a copolymer consisting of monomeric units derived from (meth) acrylic acid esters, of which from 20% to 80% by moles are the monomeric units having an oxygen-containing heterocyclic group represented by the general formula

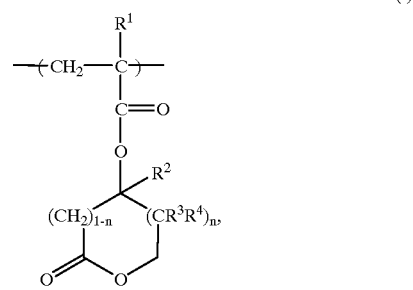

(I)

in which $R^1$ is a hydrogen atom or methyl group, $R^2$, $R^3$ and $R^4$ are each, independently from the others, a hydrogen atom, lower alkyl group having 1 to 4 carbon atoms or lower alkoxy group having 1 to 4 carbon atoms and n is 0 or 1.

The (meth)acrylic acid ester compounds, from which the the monomeric units represented by the general formula (I) given above are derived, are each a novel compound not known in the prior art.

DETAILED DESCRIPTION OF THE PREFERRED EMBODIMENTS

The component (A) in the inventive photoresist composition defined above is a specific acrylic resin of which the solubility in an aqueous alkaline solution is increased in the presence of an acid. Such an acrylic resin in general is a copolymer of monomeric compounds including (a) a derivative of (meth)acrylic acid substituted by a group capable of increasing the resistance of the resin against dry etching or an acid-dissociable protective group, (b) an ethylenically unsaturated carboxylic acid and, optionally, (c) at least one kind of other copolymerizable monomers.

Of the above mentioned three classes of the monomeric compounds, the monomeric compound of the first class (a) is a derivative of (meth)acrylic acid which can be selected from the (meth)acrylic acid derivatives conventionally used in the prior art chemical-sensitization photoresist compositions with an object to enhance the resistance of the resist layer against dry etching or to introduce acid-dissociable protective groups to the resin.

Examples of such a (meth)acrylic acid derivative belonging to the class (a) include:

(a1) acrylic or methacrylic acid substituted for the carboxylic hydrogen atom by an acid-dissociable protective group such as tert-butyl group, 2-tetrahydropyranyl group, 2-tetrahydrofuranyl group, 1-methylcyclohexyl group, 1-methyladamantyl group, 1-ethoxyethyl group and 1-methoxypropyl group as well as an ester of acrylic or methacrylic acid with 2-hydroxy-3-pinanone; and (a2) acrylic or methacrylic acid substituted for the carboxylic hydrogen atom by an acid-undissociable group such as adamantyl group, cyclohexyl group, naphthyl group, benzyl group, 3-oxocyclohexyl group, bicyclo [2.2.1] heptyl group, tricyclodecanyl group and acetonyl group as well as an ester of acrylic or methacrylic acid with terpinol.

The monomeric compound of the second class (b) is an unsaturated carboxylic acid having an ethylenic double bond and is used with an object to impart the resin with alkali solubility. Examples of such a monomeric compound include acrylic acid, methacrylic acid, maleic acid and fumaric acid, of which acrylic acid and methacrylic acid are preferred.

The monomeric compound of the third class (c) is an ethylenically unsaturated monomer having copolymerizability with the monomer of the class (a) or monomers of the classes (a) and (b). Examples of such a monomeric compound include alkyl (meth)acrylates such as methyl (meth) acrylate, ethyl (meth)acrylate, propyl (meth)acrylate, isopropyl (meth)-acrylate, n-butyl (meth)acrylate, isobutyl (meth)acrylate, n-hexyl (meth)acrylate, octyl (meth) acrylate, 2-ethylhexyl (meth)acrylate, lauryl (meth)acrylate, 2-hydroxyethyl (meth)acrylate and 2-hydroxypropyl (meth) acrylate, amides of (meth)acrylic acid such as (meth) acrylamide, N-methylol (meth)acrylamide and diacetone (meth)acrylamide, (meth)acrylonitrile, vinyl chloride and ethyl vinyl ether.

In addition to the monomeric units represented by the above given general formula (I), the acrylic resin as the component (A) in the inventive photoresist composition optionally contains the monomeric units derived from other acrylic monomers having a different oxygen-containing heterocyclic group, however, not used in the prior art for the preparation of an acrylic resin capable of being imparted with increased solubility in an aqueous alkaline solution in the presence of an acid. Examples of such acrylic monomers include the (meth)acrylic ester compounds represented by the general formulas

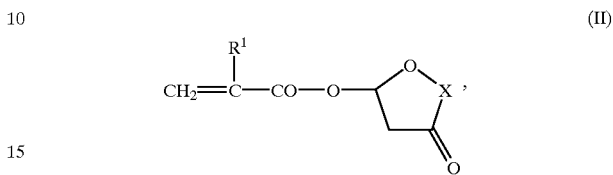

(II)

in which $R^1$ is a hydrogen atom or a methyl group and X is an alkyl-substituted or unsubstituted methylene group, and

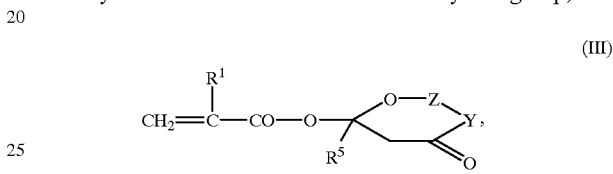

(III)

in which $R^1$ is a hydrogen atom or a methyl group, $R^5$ is a hydrogen atom or a lower alkyl group, Y is an oxygen atom or an acyl-substituted or unsubstituted methylene group and Z is an alkyl-substituted or unsubstituted methylene group or a carbonyl group.

Examples of the (meth)acrylic ester compounds represented by the above given general formula (II) include (meth)acrylic acid esters with an ester-forming group such as 2-oxacyclopentan-4-on-1-yl, 3-methyl-2-oxacyclopentan-4-on-1-yl and 3,3-dimethyl-2-oxacyclopentan-4-on-1-yl.

Examples of the (meth)acrylic acid ester compounds represented by the above given general formula (III) include (meth)acrylic acid esters with an ester-forming group such as 2,4-dioxacyclohexan-5-on-1-yl, 3-methyl-2,4-dioxacyclohexan-5-on-1-yl, 3,3-dimethyl-2,4-dioxacyclohexan-5-on-1-yl, 1-methyl-2-oxacyclohexan-3,5-dion-1-yl and 1-methyl-4-acetyl-2-oxacyclohexan-3,5-dion-1-yl.

The acrylic resin as the component (A) in the inventive photoresist composition is preferably a copolymer of a monomer mixture consisting of a monomeric compound of the class (a) with one or more of the monomeric compounds belonging to the classes (b) and (c). More preferably, the monomer mixture contains a (meth)acrylic acid substituted for the carboxylic hydroxyl group by an acid-dissociable acetal group such as 2-tetrahydropyranyl (meth)acrylate, 2-tetrahydrofuranyl (meth)acrylate, 1-ethoxyethyl (meth) acrylate and 1-methoxypropyl (meth)acrylate or, most preferably, 2-tetrahydropyranyl (meth)acrylate in respect of the high acid-dissociability and low dependency on the conditions of the post-exposure baking treatment.

It is essential that the acrylic resin as the component (A) contains the monomeric units represented by the general formula (I) in a molar fraction of 20% to 80% or, preferably 50% to 80%, the balance being the other types of the monomeric units, from the standpoint of obtaining excellent properties of the photoresist composition such as resistance against dry etching and adhesion of the resist layer to the substrate surface and contrast of patterning.

The monomeric compound, from which the monomeric units represented by the general formula (I) in the acrylic resin as the component (A), can be readily synthesized by the esterification reaction of acrylic or methacrylic acid with a hydroxyl compound having a structure of the oxygen-containing heterocyclic ring represented by the general formula

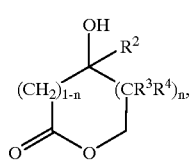

(IV)

in which each symbol has the same meaning as defined before, or an oxygen-containing heterocyclic compound represented by the general formula

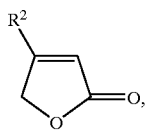

(V)

in which $R^2$ has the same meaning as defined before, according to a conventional method of esterification.

Examples of the compounds used in the above mentioned reactions include 3-hydroxy-1-oxacyclopentan-2-one, 4-methyl-3-hydroxy-1-oxacyclopentan-2-one, 4,4-dimethyl-3-hydroxy-1-oxacyclopentan-2-one, 3-methyl-3-hydroxy-1-oxacyclopentan-2-one and 4-methoxy-1-oxacyclopentan-3-en-2-one. Preferable compounds of the general formula (IV) are those having a hydrogen atom or methyl group as each of the groups $R^2$, $R^3$ and $R^4$, of which 4,4-dimethyl-3-hydroxy-1-oxacyclopentan-2-one is more preferable, and a preferable compound of the general formula (V) is that having a methoxy group as $R^2$.

The radiation-sensitive acid-generating agent as the component (B) in the inventive chemical-sensitization photoresist composition can be selected from those used as the acid-generating compound in chemical-sensitization photoresist compositions of the prior art without particular limitations. Examples of suitable acid-generating compounds includes the following compounds classified into classes (1) to (7):

(1) bissulfonyl diazomethane compounds such as bis(p-toluenesulfonyl) diazomethane, bis(1,1-dimethylethylsulfonyl) diazomethane, bis(cyclohexylsulfonyl)diazomethane and bis(2,4-dimethylphenylsulfonyl)diazomethane;

(2) nitrobenzyl compounds such as 2-nitrobenzyl p-toluenesulfonate and 2,6-dinitrobenzyl p-toluenesulfonate;

(3) sulfonic acid esters such as pyrogallol trimesylate and pyrogallol tritosylate;

(4) onium salt compounds such as diphenyliodonium hexafluorophosphate, (4-methoxyphenyl) phenyliodonium trifluoromethane sulfonate, bis(p-tert-butylphenyl)iodonium trifluoromethane sulfonate, triphenylphosphonium hexafluorophosphate, (4-methoxyphenyl)diphenylsulfonium trifluoromethane sulfonate and (p-tert-butylphenyl) diphenylsulfonium trifluoromethane sulfonate;

(5) alkyl-substituted or unsubstituted benzoin tosylate compounds such as benzoin tosylate and α-methylbenzoin tosylate;

(6) halogen-containing triazine compounds such as 2-(4-methoxyphenyl)-4,6-bis(trichloromethyl)-1,3,5-triazine, 2-(4-methoxynaphthyl)-4,6-bis(trichloromethyl)-1,3,5-triazine, 2[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis(trichloromethyl)-1,3,5-triazine, 2,4,6-tris(2,3-dibromopropyl)-1,3,5-triazine and tris(2,3-dibromopropyl) isocyanurate; and (7) cyano group-containing oximesulfonate compounds such as
α-(methylsulfonyloxyimino)phenyl acetonitrile,
α-(methylsulfonyloxyimino)-4-methoxyphenyl acetonitrile,
α-(trifluoromethylsulfonyloxyimino)phenyl acetonitrile,
α-(trifluoromethylsulfonyloxyimino)-4-methoxyphenyl acetonitrile,
α-(ethylsulfonyloxyimino)-4-methoxyphenyl acetonitrile,
α-(propylsulfonyloxyimino)-4-methylphenyl acetonitrile,
α-(methylsulfonyloxyimino)-4-bromophenyl acetonitrile,
α-(methylsulfonyloxyimino)-1-cyclopentenyl acetonitrile,
α-(1- or 2-naphthylsulfonyloxyimino)-4-methoxybenzyl cyanide and α-(10-canphorsulfonyloxyimino)-4-methoxybenzyl cyanide; of which the onium salt compounds and the cyano group-containing oximesulfonate compounds are particularly preferable.

The amount of the acid-generating agent as the component (B) in the inventive photoresist composition is in the range from 0.5 to 30 parts by weight or, preferably, from 1 to 10 parts by weight per 100 parts by weight of the acrylic resin as the component (A). When the amount of the component (B) is too small, no practical patterning of the resist layer can be accomplished while, when the amount of the component (B) is increased to exceed the upper limit, a photoresist composition in the form of a uniform solution cannot be obtained or the storage stability of the photoresist solution is decreased.

It is of course optional according to need that the chemical-sensitization photoresist composition of the present invention is admixed with various kinds of additives used in the conventional chemical-sensitization photoresist compositions in the prior art including halation inhibitors, antioxidants, heat stabilizers, adhesion improvers, plasticizers, coloring agents, surface active agents, auxiliary resins, carboxylic acids and amine compounds each in a limited amount.

The photoresist composition of the present invention is used usually in the form of a uniform solution prepared by dissolving the above described essential and optional ingredients in an organic solvent. Examples of suitable organic solvents include ketone solvents such as acetone, methyl ethyl ketone, cyclohexanone, methyl isoamyl ketone and 2-heptanone, polyhydric alcohols and derivatives thereof such as ethyleneglycol, ethyleneglycol monoacetate, propyleneglycol, propyleneglycol monoacetate, dipropyleneglycol and dipropyleneglycol monoacetate as well as monomethyl, monoethyl, monopropyl, monobutyl and monophenyl ethers thereof, cyclic ethers such as dioxane, and ester solvents such as methyl acetate, ethyl acetate, butyl acetate, methyl pyruvate, ethyl pyruvate, methyl methoxypropionate and ethyl ethoxypropionate. These organic solvents can be used either singly or as a mixture of two kinds or more according to need.

Following is a typical procedure for the photlithographic patterning by using the chemical-sensitization photoresist composition of the present invention. Thus, a substrate such as a semiconductor silicon wafer is uniformly coated with the photoresist composition in the form of a uniform solution and the coating layer is subjected to a pre-baking treatment at a temperature of 70 to 150° C. for 30 to 150 seconds to form a photoresist layer on the substrate surface, which is pattern-wise exposure to actinic rays such as ArF excimer laser beams through a pattern-bearing photomask to form a latent image of the pattern in the resist layer followed by a post-exposure baking treatment at a temperature of 70 to 150° C. for 30 to 150 seconds. Thereafter, the latent image formed in the resist layer is developed by using an aqueous alkaline solution, such as an aqueous solution of tetramethylammonium hydroxide and choline, as the developer so as to dissolve away the resist layer in the pattern-wise exposed areas leaving the resist layer in the unexposed areas.

In the following, the present invention is described in more detail by way of Examples as preceded by the description of the procedure for the preparation of the specific acrylic resin used as the component (A) of the photoresist composition. In the Examples given below, the term of "parts" always refers to "parts by weight".

Preparation 1.

A mixture was prepared by dissolving 70.2 g (0.54 mole) of 4,4-dimethyl-3-hydroxy-1-oxacyclopentan-2-one and 60 g (0.60 mole) of triethylamine in 200 ml of tetrahydrofuran and, then, 62.4 g (0.60 mole) of methacryloyl chloride were added dropwise to the mixture at 25° C. under agitation over a period of 1 hour to give a reaction mixture.

After further continued agitation for 24 hours at 25° C., the reaction mixture was filtered and the filtrate was distilled to remove the solvent. The residue was dissolved in 300 ml of diethyl ether and the solution was repeatedly washed 10 times with a 10% by weight aqueous solution of sodium hydroxide. The reaction product contained in this solution was purified by column chromatography with n-heptane as the eluant to give a colorless liquid which could be identified by analysis to be a methacrylic acid ester of the compound expressed by the structural formula

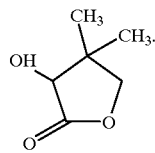

The $^1$H-NMR spectrum of this compound taken with acetone $d_6$ as the solvent had peaks corresponding to the δ values of 1.15 ppm, 1.25 ppm, 1.92 ppm, 4.10 ppm, 5.50 ppm, 5.62 ppm and 6.12 ppm.

A polymerization mixture was prepared by dissolving 20.0 g (0.094 mole) of the thus prepared methacrylic acid ester and 5.3 g (0.031 mole) of 2-tetrahydropyranyl methacrylate in 150 g of tetrahydrofuran with addition of 0.82 g of azobisisobutyronitrile as a polymerization initiator and the polymerization mixture was heated at 75° C. for 3 hours under agitation to effect polymerization of the monomers. After completion of the polymerization reaction, the polymerization mixture was poured into 5 liters of n-heptane to precipitate the polymer, referred to as the copolymer A1 hereinafter, which was taken by filtration and dried at room temperature under reduced pressure. The yield of the copolymer A1 was 15.0 g. The copolymer A1 had a weight-average molecular weight of 14000 with a dispersion of the molecular weight distribution of 1.90.

Preparation 2.

A mixture was prepared by dissolving 55.1 g (0.54 mole) of 3-hydroxy-1-oxacyclopentan-2-one and 60 g (0.60 mole) of triethylamine in 200 ml of tetrahydrofuran and, then, 62.4 g (0.60 mole) of methacryloyl chloride were added dropwise to the mixture at 25° C. under agitation over a period of 1 hour to give a reaction mixture.

After further continued agitation for 24 hours at 25° C. the reaction mixture was filtered and the filtrate was distilled to remove the solvent. The residue was dissolved in 300 ml of diethyl ether and the solution was repeatedly washed 10 times with a 10% by weight aqueous solution of sodium hydroxide. The reaction product contained in this solution was purified by column chromatography with n-heptane as the eluant to give a colorless liquid which could be identified by analysis to be a methacrylic acid ester of the compound expressed by the structural formula

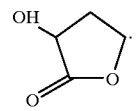

The $^1$H-NMR spectrum of this compound taken with acetone $d_6$ as the solvent had peaks corresponding to the δ values of 1.92 ppm, 2.30 to 2.50 ppm, 3.90 to 4.10 ppm, 5.20 ppm, 5.60 ppm and 6.12 ppm.

A polymerization mixture was prepared by dissolving 17.4 g (0.094 mole) of the thus prepared methacrylic acid ester and 5.3 g (0.031 mole) of 2-tetrahydropyranyl methacrylate in 560 g of tetrahydrofuran with addition of 0.81 g of azobisisobutyronitrile as a polymerization initiator and the polymerization mixture was heated at 75° C. for 3 hours under agitation to effect polymerization of the monomers. After completion of the polymerization reaction, the polymerization mixture was poured into 5 liters of n-heptane to precipitate the polymer, referred to as the copolymer A2 hereinafter, which was taken by filtration and dried at room temperature under reduced pressure. The yield of the copolymer A2 was 14.9 g. The copolymer A2 had a weight-average molecular weight of 13500 with a dispersion of the molecular weight distribution of 2.01.

Preparation 3.

A mixture was prepared by dissolving 62.6 g (0.54 mole) of 4-methoxy-1-oxacyclopent-3-en-2-one in 200 ml of tetrahydrofuran and, then, 112 g (1.08 mole) of methacryloyl chloride were added thereto under agitation to give a reaction mixture.

Thereafter, 0.3 g of para-toluene sulfonic acid was added to the reaction mixture which was further agitated for 4 hours at 25° C. The reaction mixture was dissolved in 300 ml of diethyl ether and repeatedly washed 10 times with a 10% by weight aqueous solution of sodium hydroxide. The reaction product contained in this solution was purified by column chromatography with n-heptane as the eluant to give a colorless liquid which could be identified by analysis to be a methacrylic acid ester of the compound expressed by the structural formula

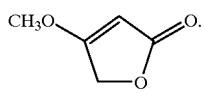

The $^1$H-NMR spectrum of this compound taken with acetone $d_6$ as the solvent had peaks corresponding to the δ values of 1.92 ppm, 2.30 to 2.80 ppm, 3.80 ppm, 5.65 ppm and 6.12 ppm.

A polymerization mixture was prepared by dissolving 20.2 g (0.094 mole) of the thus prepared methacrylic acid ester and 5.3 g (0.031 mole) of 2-tetrahydropyranyl methacrylate in 560 g of tetrahydrofuran with addition of 0.81 g of azobisisobutyronitrile as a polymerization initiator and the polymerization mixture was heated at 75° C. for 3 hours under agitation to effect polymerization of the monomers. After completion of the polymerization reaction, the polymerization mixture was poured into 5 liters of n-heptane to precipitate the polymer, referred to as the copolymer A3 hereinafter, which was taken by filtration and dried at room temperature under reduced pressure. The yield of the copolymer A3 was 15.5 g. The copolymer A3 had a weight-average molecular weight of 14000 with a dispersion of the molecular weight distribution of 2.10.

Preparation 4.

A mixture was prepared by dissolving 62.6 g (0.54 mole) of 3-hydroxy-3-methyl-1-oxacyclopentan-2-one and 60 g (0.60 mole) of triethylamine in 200 ml of tetrahydrofuran and, then, 62.4 g (0.60 mole) of methacryloyl chloride were added dropwise to the mixture at 25° C. under agitation over a period of 1 hour to give a reaction mixture.

After further continued agitation for 24 hours at 25° C. the reaction mixture was filtered and the filtrate was distilled to remove the solvent. The residue was dissolved in 300 ml of diethyl ether and the solution was repeatedly washed 10 times with a 10% by weight aqueous solution of sodium hydroxide. The reaction product contained in this solution was purified by column chromatography with n-heptane as the eluant to give a colorless liquid which could be identified by analysis to be a methacrylic acid ester of the compound expressed by the structural formula

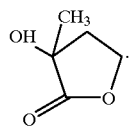

The $^1$H-NMR spectrum of this compound taken with acetone $d_6$ as the solvent had peaks corresponding to the δ values of 1.80 ppm, 1.92 ppm, 2.30 to 2.50 ppm, 3.90 to 4.10 ppm, 5.65 ppm and 6.12 ppm.

A polymerization mixture was prepared by dissolving 18.7 g (0.094 mole) of the thus prepared methacrylic acid ester and 5.3 g (0.031 mole) of 2-tetrahydropyranyl methacrylate in 560 g of tetrahydrofuran with addition of 0.81 g of azobisisobutyronitrile as a polymerization initiator and the polymerization mixture was heated at 75° C. for 3 hours under agitation to effect polymerization of the monomers. After completion of the polymerization reaction, the polymerization mixture was poured into 5 liters of n-heptane to precipitate the polymer, referred to as the copolymer A4 hereinafter, which was taken by filtration and dried at room temperature under reduced pressure. The yield of the copolymer A4 was 15.0 g. The copolymer A4 had a weight-average molecular weight of 12000 with a dispersion of the molecular weight distribution of 1.85.

Preparation 5.

A copolymer of adamantyl methacrylate expressed by the structural formula

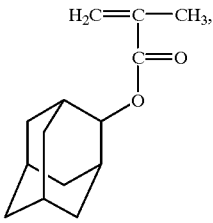

2-tetrahydropyranyl methacrylate and methacrylic acid, referred to as the copolymer A5 hereinafter, was prepared by conducting, in the same manner as in Preparation 1 described above, the polymerization reaction of a monomer mixture of these three kinds of monomeric compounds of which the molar fractions of adamantyl methacrylate, 2-tetrahydropyranyl methacrylate and methacrylic acid were 50%, 45% and 5%, respectively. The yield of the copolymer A5 was 16.0 g. The copolymer A5 had a weight-average molecular weight of 16500 with a dispersion of the molecular weight distribution of 2.20.

Preparation 6.

A copolymer of a methacrylic acid ester compound expressed by the structural formula

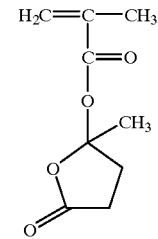

and 2-tetrahydropyranyl methacrylate, referred to as the copolymer A6 hereinafter, was prepared by conducting, in the same manner as in Preparation 1 described above, the polymerization reaction of a monomer mixture consisting of 17.2.g (0.094 mole) of the monomeric compound of the above given structural formula and 5.3 g (0.031 mole) of 2-tetra-hydropyranyl methacrylate. The yield of the copolymer A6 was 14.7 g. The copolymer A6 had a weight-average molecular weight of 14500 with a dispersion of the molecular weight distribution of 1.98.

Example 1.

A chemical-sensitization positive-working photoresist solution was prepared by dissolving 100 parts of the copolymer A1 prepared in Preparation 1 and 2 parts of bis(4-tert-butylphenyl) iodonium trifluoromethane sulfonate in 680 parts of propyleneglycol monomethyl ether acetate.

This photoresist solution was uniformly applied onto a semiconductor silicon wafer by using a spinner and dried by heating for 90 seconds on a hot plate at 100° C. to form a photoresist layer having a thickness of 0.5 μm.

The photoresist layer was pattern-wise exposed to ArF excimer laser beams of 193 nm wavelength on an ArF excimer laser exposure machine (manufactured by Nikon Co.) followed by a post-exposure baking treatment at 110° C. for 90 seconds and then subjected to a puddle development treatment in a 2.38% by weight aqueous solution of tetramethylammonium hydroxide taking 65 second at 23° C.

The minimum exposure dose required for obtaining a line-and-space patterned resist layer with a line:space width ratio of 1:1 by using a line-and-space photomask pattern of 0.25 μm line width was 5.0 mJ/cm$^2$ as a measure of the photosensitivity of the photoresist composition.

Further, the cross sectional profile of the thus formed line-patterned resist layer of 0.25 μm line width was excellently orthogonal standing upright on the substrate surface as examined on a scanning electron microscopic photograph.

The resist layer on the substrate surface was subjected to a dry etching treatment with tetrafluoromethane as the etching gas on a dry-etching instrument (Model OAPM-406, manufactured by Tokyo Ohka Kogyo Co.) to find that the rate of film thickness decrease per unit time, as a measure of the resistance against dry etching, was 1.1 relative to the rate of film thickness decrease of a polyhydroxystyrene layer taken as 1.0. Patterning resolution was so high that a line pattern of 0.20 μm line width could be fully reproduced without pattern falling.

Example 2.

The experimental procedure was substantially the same as in Example 1 excepting for the replacement of the copolymer A1 with the same amount of the copolymer A2 prepared in Preparation 2. The results of the evaluation tests were that the minimum exposure dose representing the photosensitivity was 6.0 mJ/cm$^2$, the cross sectional profile of the line-patterned resist layer of 0.25 μm width was excellently orthogonal standing upright on the substrate surface and the relative resistance against dry etching was 1.1. Patterning resolution was so high that a line pattern of 0.20 μm line width could be fully reproduced without pattern falling.

Example 3.

The experimental procedure was substantially the same as in Example 1 excepting for the replacement of the copolymer A1 with the same amount of the copolymer A3 prepared in Preparation 3. The results of the evaluation tests were that the minimum exposure dose representing the photosensitivity was 5.5 mJ/cm$^2$, the cross sectional profile of the line-patterned resist layer of 0.25 μm width was excellently orthogonal standing upright on the substrate surface and the relative resistance against dry etching was 1.1. Patterning resolution was so high that a line pattern of 0.20 μm line width could be fully reproduced without pattern falling.

Example 4.

The experimental procedure was substantially the same as in Example 1 excepting for the replacement of the copolymer A1 with the same amount of the copolymer A4 prepared in Preparation 4. The results of the evaluation tests were that the minimum exposure dose representing the photosensitivity was 5.0 mJ/cm$^2$, the cross sectional profile of the line-patterned resist layer of 0.25 μm width was excellently orthogonal standing upright on the substrate surface and the relative resistance against dry etching was 1.2. Patterning resolution was so high that a line pattern of 0.20 μm line width could be fully reproduced without pattern falling.

Comparative Example 1.

The experimental procedure was substantially the same as in Example 1 excepting for the replacement of the copolymer A1 with the same amount of the copolymer A5 prepared in Preparation 5. The results of the evaluation tests were that the minimum exposure dose representing the photosensitivity was 15 mJ/cm$^2$ and the relative resistance against dry etching was 1.0. Patterning resolution was not so high that a line pattern of 0.30 μm or finer line width could not be completely reproduced.

Comparative Example 2.

The experimental procedure was substantially the same as in Example 1 excepting for the replacement of the copolymer A1 with the same amount of the copolymer A6 prepared in Preparation 6. The results of the evaluation tests were that the minimum exposure dose representing the photosensitivity was 5.0 mJ/cm$^2$ and patterning resolution was so high that a line pattern of 0.25 μm line width could be fully reproduced without pattern falling. However, the cross sectional profile of the line-patterned resist layer of 0.30 μm width was not orthogonal but trapezoidal. The relative resistance against dry etching was 1.5.

What is claimed is:

1. Methacrylic acid ester of 3-hydroxy-3-methyl-1-oxacyclopentan-2-one expressed by the structural formula

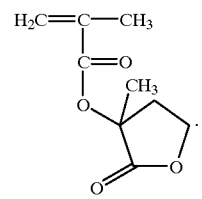

2. A chemical-sensitization positive-working photoresist composition which comprises, as a uniform solution in an organic solvent:
   (A) 100 parts by weight of an acrylic resin of which the solubility in an aqueous alkaline solution is subject to an increase in the presence of an acid; and
   (B) from 0.5 to 30 parts by weight of a radiation-sensitive acid-generating agent capable of releasing an acid when irradiated with actinic rays,
   the acrylic resin as the component (A) being a copolymer comprising the monomeric units having an oxygen-containing heterocyclic group represented by the formula:

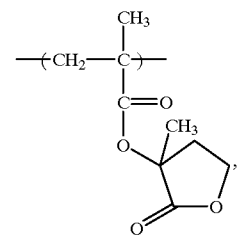

in a molar fraction in the range of from 20 to 80 percent of the overall monomeric units.

3. A method for patterning which comprises applying the chemical-sensitization positive-working photoresist composition of claim 2 to a substrate and exposing said photoresist to pattern-wise actinic irradiation and developing the pattern-wise exposed photoresist layer.

4. The method according to claim 3 wherein the actinic irradiation is an ArF excimer laser beam.

* * * * *